US00PP13674P29

(12) United States Plant Patent

Schlueter

(10) Patent No.: US PP13,674 P2

(45) Date of Patent: Mar. 25, 2003

(54) *HIBISCUS ROSA-SINENSIS* PLANT NAME 'AMAZON QUEEN'

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/152,944

(22) Filed: May 22, 2002

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—W C Haas
(74) *Attorney, Agent, or Firm*—Christie, Parker & Hale, LLP

(57) ABSTRACT

A new plant variety of *Hibiscus Rosa-sinensis* named 'AMAZON QUEEN', characterized by a large ruffled coppery orange flower with a white "eye." It is a free-flowering plant with an upright, compact habit. The foliage is glossy and dark green.

4 Drawing Sheets

BACKGROUND OF THE INVENTION

The present invention relates to a new and distinct variety of *Hibiscus Rosa-sinensis* L., which was developed in a controlled breeding program in Webster, Tex. by the originator Mr. Barry Schlueter. The varietal denomination of the new variety is 'AMAZON QUEEN'.

The genus Hibiscus comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. Hibiscus is included in the family Malvaceae, which comprises about 95 genera of herbs, shrubs and trees originating in tropical and temperate regions. *Hibiscus Rosa-sinensis* is a glabrate shrub, seldom over 8 feet tall in cultivation, but treelike to 15 feet or more in tropical regions. Leaves to 6 inches long, ovate, usually serrate, mostly glossy green. Flowers solitary in upper leaf axils.

The new Hibiscus is a product of a planned breeding program conducted by the inventor in Webster, Tex. The objective of the program was to create new Hibiscus selections with improved bloom quality, color and floriferousness, plants that can be commercially produced on their own root systems, and improved plant habit with regard to vigor and post-production longevity.

SUMMARY OF THE INVENTION

The new variety was discovered in a controlled breeding program of *Hibiscus Rosa-sinensis* and differs from its parents and other known cultivars of *Hibiscus Rosa-sinensis* by the following characteristics in combination:

1. Upright, compact symmetrical plant habit that is suitable for container production;
2. Healthy green foliage;
3. Vigorous growth habit;
4. Large unique multi-colored flowers with predominantly orange petals and a red to pink fading center; and
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER VARIETIES

'AMAZON QUEEN' is distinguished from its female parent 'SCHIZOPHRENIC' (unpatented) by having a more upright habit and its extremely fancy flower that is heavily ruffled and tufted; 'SCHIZOPHRENIC' has a low growing habit and its flower is a blend of yellow, orange and pink. 'AMAZON QUEEN' is distinguished from its male parent 'LADY EMMA' (unpatented) by its improved branching habit and flower form. 'LADY EMMA' is extremely upright, sending out very few lateral branches, and its bloom is so heavily textured that it often fails to open properly.

Plants of 'AMAZON QUEEN' can be compared to plants of the cultivar 'GREAT SATAN' (unpatented). However, in side-by-side comparisons conducted in Webster, Tex., plants of the new cultivar differ from plants of the cultivar 'GREAT SATAN' in the following characteristics:

1. Flower color of 'AMAZON QUEEN' are brighter in color than flowers of 'GREAT SATAN';
2. Plants of 'AMAZON QUEEN' are easier to clone via rooting than plants of the cultivar 'GREAT SATAN'; and
3. Plants of 'AMAZON QUEEN' possess healthier foliage and a better growth habit than the cultivar 'GREAT SATAN'.

BRIEF DESCRIPTION OF ILLUSTRATIONS

The accompanying illustrations show a specimen of the new cultivar in a photographic illustration as true to color as is reasonably possible to make in an illustration of this character.

DESCRIPTION OF THE NEW VARIETY

Figure 1:
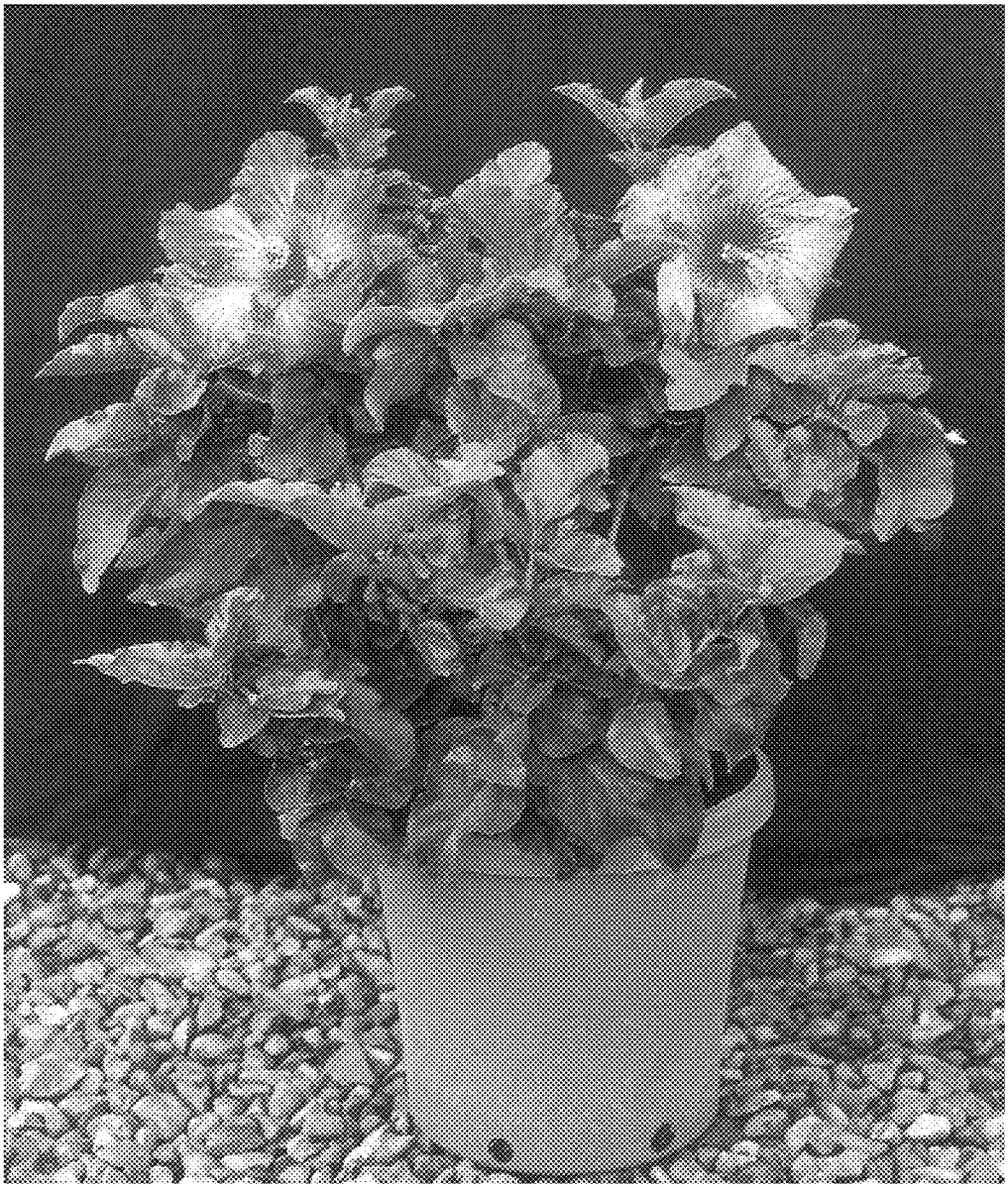
FIG. 1 illustrates a side perspective view of a typical plant of 'AMAZON QUEEN'.
Figure 2:
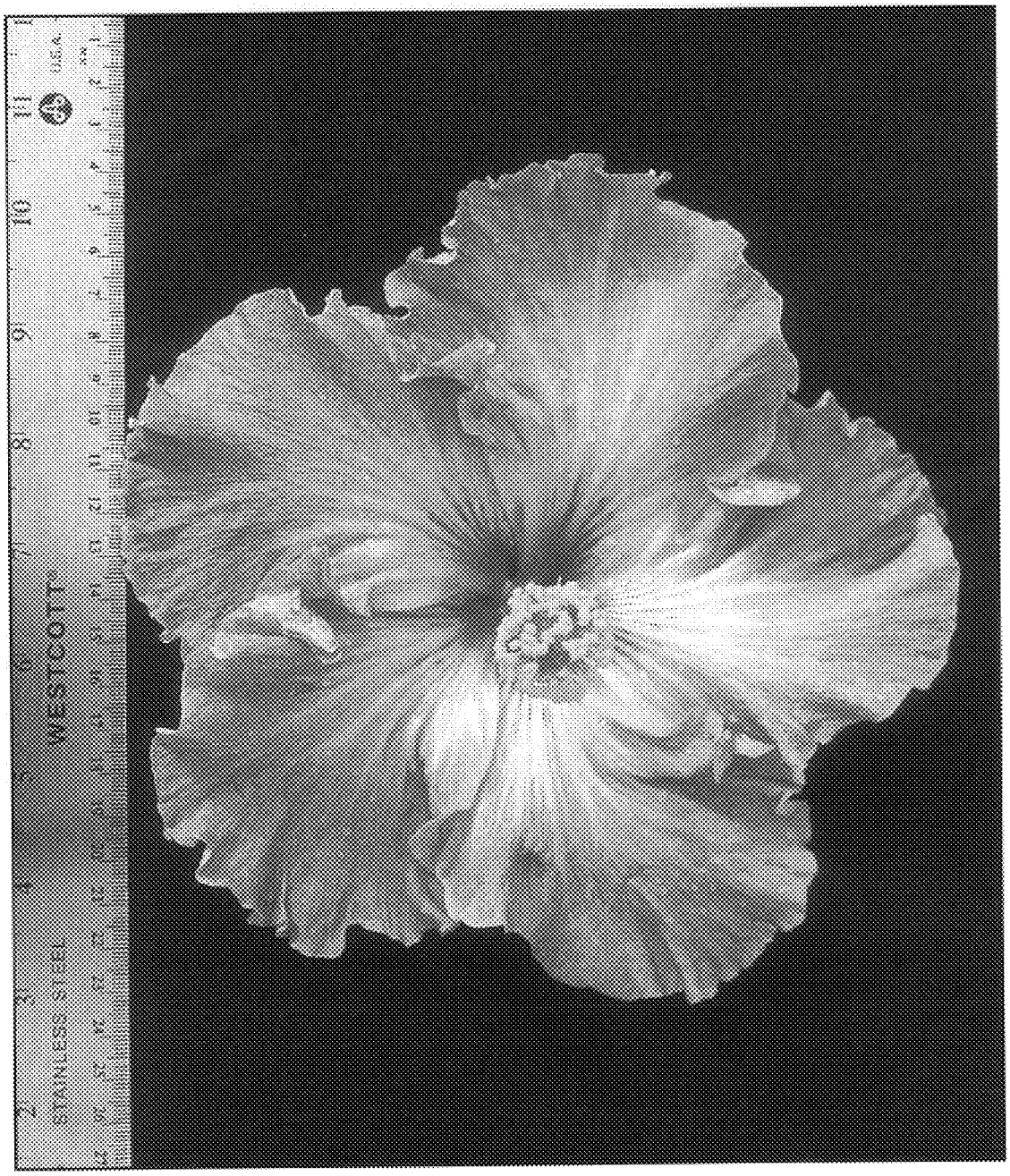
FIG. 2 illustrates the scale of a typical flower of 'AMAZON QUEEN'.
Figure 3:
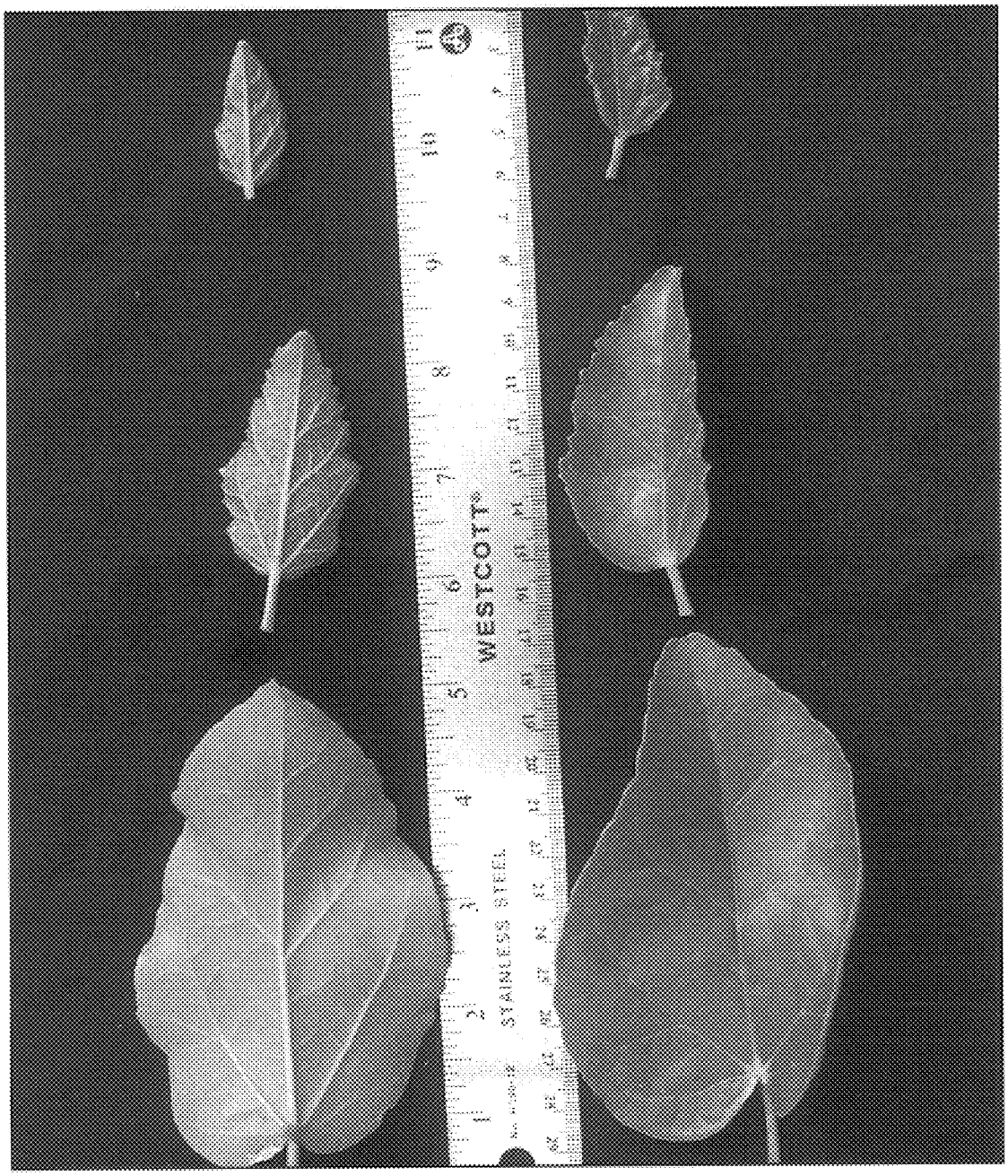
FIG. 3 illustrates the typical young to mature foliage of 'AMAZON QUEEN'; the abaxial and adaxial surfaces are shown at each stage.
Figure 4:
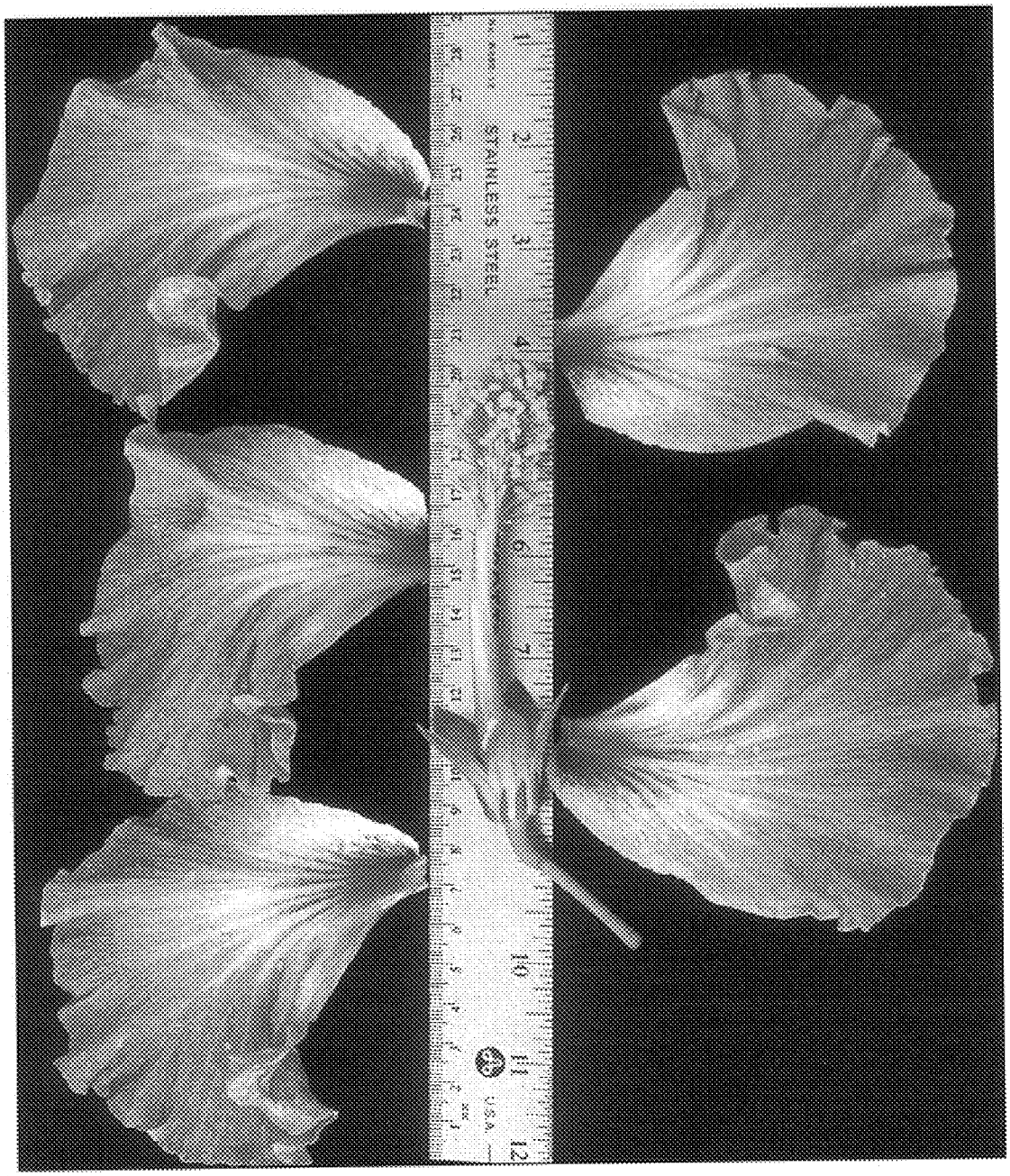
FIG. 4 illustrates a dissected flower of 'AMAZON QUEEN', including shape and size of petals and characteristics of the reproductive structures.

'AMAZON QUEEN' has not been observed under all possible environmental, cultural and light conditions. The following observations and descriptions are of plants grown in Fulshear, Tex., in October 2001, under polypropylene shadecloth providing a 30% light reduction, and under conditions which closely approximate commercial production. Plants described were approximately 1-year old and in a Number 3 nursery container.

In this description, color references are to *The Royal Horticultural Society Colour Chart* (1995) and terminology used in the color descriptions herein refers to plate numbers in this color chart. Phenotypic expression may vary with light intensity, cultural and environmental conditions.

Classification:

*Botanical.*—*Hibiscus Rosa-Sinensis* L. 'AMAZON QUEEN'.

*Parentage.*— *Female: Hibiscus Rosa-sinensis* 'SCHIZOPHRENIC' (unpatented). Male: *Hibiscus Rosa-sinensis* 'LADY EMMA' (unpatented).

*Propagation.*—By stem cuttings.

*Time to initiate rooting.*—Approximately 14 to 21 days at 21° to 24° C.

*Time to develop roots.*—Approximately 42 to 56 days at 21° to 24° C.

*Root description.*—Fine to medium; fibrous; freely branching.

Plant:

*Size.*—Height: Approximately 51 cm from soil level to top of flowers. Diameter/Spread: Approximately 60 cm.

*Form & growth habit.*—Perennial, evergreen shrub; mostly upright and somewhat spreading.

*Branching.*—Freely branching; approximately 4 to 8 lateral branches develop after pinching. Lateral Branches: Approximately 20 cm long and 5 mm in diameter. Internode Length: Approximately 4 cm.

Leaf:

*Shape.*—Cordate. Apex: Rounded. Base: Cordate.

*Leaf size.*—Approximately 10 cm long and 10 cm wide.

*Arrangement.*—Alternate, single; symmetrical.

*Margin.*—Undulate with crenulate margins.

*Aspect.*—Undulate.

*Texture/substance.*—Glabrous, shiny.

*Coloration.*—Young Foliage Upper side: Near Yellow-Green Group 144A. Underside: Near Yellow-Green Group 144B. Mature Foliage Upper side: Near Green Group 137A. Underside: Near Green Group 137D.

*Petioles.*—Size: Approximately 3 cm long, 3 mm across. Coloration: Near Yellow-Green Group 144B. Texture: Smooth.

*Hardiness.*—USDA Zone 10 (30° F. to 40° F.).

*Pests/diseases.*—Resistance to known Hibiscus diseases had not been observed on plants grown under conditions approximating commercial practices.

Infloresence:

*Bloom period.*—Typically year-round under subtropical and tropical conditions.

*Flower arrangement.*—Arranged singly at terminal leaf axils; free-flowering with 3 to 4 flower buds and/or open flowers per terminal apex; flowers face upright and slightly outward.

*Flower appearance.*—Ruffled orange petals with a red "eye" or throat fading to pink and white; flowers are open for about 2 days before closing; flowers persistent.

Buds (just prior to showing color):

*Rate of opening.*—Approximately 1 or 2 days, depending on temperature. Shape: Elliptic. Length: Approximately 3 cm. Diameter: Approximately 1.4 cm. Color: Near Yellow-Green Group 144A.

*Fragrance.*—None noted.

*Petals.*—Number/Arrangement: Corolla consists of 5 overlapping petals. Shape: Spatulate with rounded apex. Size: Approximately 10 cm long and 10 cm wide. Margin: Entire, but ruffled. Texture: Smooth.

*Color.*—Upper Surface: The "eye" or throat starts at near Red Group 46A and fades outward to near Red Group 49A and eventually White Group 155A; the outer half of the petal is near Orange Group 26A. Lower Surface: The majority is near Yellow-Orange Group 20B to 20C, eventually fading to near White Group 155B at the base of the petal.

*Sepals.*—Number/Arrangement: 5 sepals fused into a star-shaped calyx. Shape: Linear with acuminate apices. Margin: Entire. Color: Near Yellow-Green Group 144A.

*Peduncles.*—Length: Approximately 4 cm. Diameter: Approximately 2 mm. Angle: Upright to about 45°. Strength: Strong, flexible. Color: Near Yellow-Green Group 144B.

Reproductive organs:

*Androecium.*—Stamens: Numerous; about 50. Length: Approximately 5 mm. Filament Color: Near Red Group 49A. Anther size: Approximately 1 mm. Pollen amount: Abundant. Pollen color: Yellow-Orange Group 15B.

*Gynoecium.*—Pistil Length: 8 cm. Stigma appearance: 5; rounded. Stigma diameter: Approximately 2 mm. Stigma color: Near Orange-Red Group 34A. Style color: Lower third near Orange Group 27C; mid-third near Red Group 49B; upper-third near Red Group 49A.

*Seed production.*—Seed production has not been observed.

I claim:

1. A new plant variety of *Hibiscus Rosa-sinensis* of the variety substantially as shown and described.

* * * * *